(12) United States Patent
Pennemann et al.

(10) Patent No.: US 9,346,012 B2
(45) Date of Patent: May 24, 2016

(54) METHOD AND APPARATUS FOR DENENOXING WASTE GASES FROM NITRATION

(71) Applicants: Bayer MaterialScience LLC, Pittsburgh, PA (US); Bayer MaterialScience AG, Leverkusen (DE)

(72) Inventors: Bernd Pennemann, Bergisch Gladbach (DE); Ulrich Westphal, Leverkusen (DE); Dieter Foertsch, Leichlingen (DE); Spotswood Miller, Friendswood, TX (US)

(73) Assignees: Covestro LLC, Pittsburgh, PA (US); Covestro Deutschland AG, Leverkusen (DE)

(*) Notice: Subject to any disclaimer, the term of this patent is extended or adjusted under 35 U.S.C. 154(b) by 0 days.

(21) Appl. No.: 14/300,504

(22) Filed: Jun. 10, 2014

(65) Prior Publication Data

US 2015/0352488 A1    Dec. 10, 2015

(51) Int. Cl.
| | |
|---|---|
| C07C 209/00 | (2006.01) |
| B01D 53/56 | (2006.01) |
| B01D 53/77 | (2006.01) |
| C07C 209/32 | (2006.01) |
| C07C 209/76 | (2006.01) |
| C07C 201/08 | (2006.01) |
| C07C 209/36 | (2006.01) |

(52) U.S. Cl.
CPC ............ B01D 53/56 (2013.01); B01D 53/77 (2013.01); C07C 201/08 (2013.01); C07C 209/32 (2013.01); C07C 209/36 (2013.01); C07C 209/76 (2013.01)

(58) Field of Classification Search
CPC .................... C07C 209/365; C07C 205/12
USPC .......................................... 564/417; 423/173
See application file for complete search history.

(56) References Cited

U.S. PATENT DOCUMENTS

| | | | |
|---|---|---|---|
| 4,115,515 A | 9/1978 | Tenner et al. | |
| 4,740,621 A | 4/1988 | Adams et al. | |
| 4,956,161 A | 9/1990 | Cahn et al. | |
| 5,441,401 A * | 8/1995 | Yamaguro et al. | B01D 53/9431 431/2 |
| 2006/0198779 A1 | 9/2006 | Hurst et al. | |
| 2010/0160685 A1 | 6/2010 | Ritter et al. | |
| 2012/0228218 A1 | 9/2012 | Fritz et al. | |
| 2013/0197268 A1 | 8/2013 | Knauf et al. | |

FOREIGN PATENT DOCUMENTS

EP    0803278 A1    10/1997

OTHER PUBLICATIONS

Reference Document on Best Available Techniques for Large Combustion Plants, European Commission, Jul. 2006, pp. 106-114, 116.*
Kolb, T., Jansohn, P., & Leuckel, W., Reduction of NOx Emissions in Turbulent Combustion by Fuel-Staging / Effects of Mixing and Stochimetry in the Reduction Zone, Proceedings of the Combustion Institute, 22, 1988, p. 1193-1203.
Greul, U., Experimentelle Untersuchung feuerungstechnishcer NOx-Minderungsmaβnahmen bei der Kohlenstaubverbrennung. Düsseldorf: VDI Verlag GmbH, 1988, pp. 140-145.
Reference Document on Best Available Techniques for the Manufacture of Large Volume Inorganic Chemicals-Ammonia, Acids and Fertilisers, European Commission, Aug. 2007, pp. 97-99, 117-120 and 135-136.
Reference Document on Best Available Techniques for Large Combustion Plants, European Commission, Jul. 2006, pp. 106-114 and 116.

* cited by examiner

*Primary Examiner* — Porfirio Nazario Gonzalez
*Assistant Examiner* — Kofi Adzamli
(74) *Attorney, Agent, or Firm* — Donald R. Palladino; Robert S. Klemz

(57) ABSTRACT

The invention relates to a method for reducing the concentration of nitrogen oxides in waste gases released dating the production of organic amino compounds, wherein an organic compound is first reacted with $NO_x$ and/or nitric acid to form an organic nitro compound with the formation of an $NO_x$-containing waste gas stream and the organic nitro compound is converted to the organic ammo compound by means of hydrogen-containing reaction gas, the reaction of the organic nitro compound with the hydrogen-containing reduction gas taking place with the formation of a hydrogen-containing waste gas stream, the method being characterised in that the $NO_x$-containing waste gas stream is combined with the hydrogen-containing waste gas stream and/or an externally supplied hydrogen stream and is reacted at a temperature of 800 to 1700° C. for the at least partial reduction of the $NO_x$ concentration. The invention additionally relates to an apparatus for carrying out the method.

14 Claims, 1 Drawing Sheet

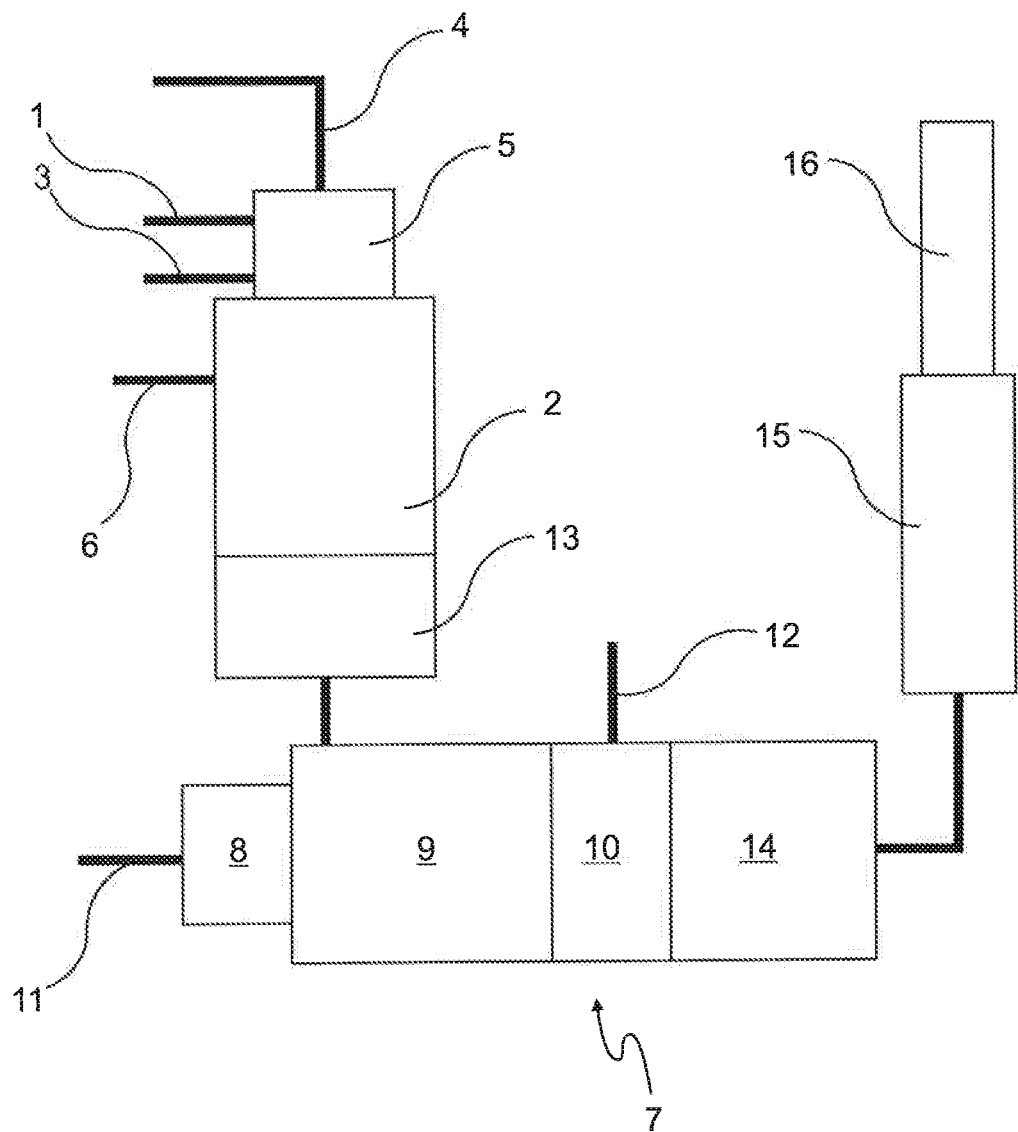

METHOD AND APPARATUS FOR DENENOXING WASTE GASES FROM NITRATION

BACKGROUND OF THE INVENTION

The invention relates to a method for reducing the concentration of nitrogen oxides in waste gases released during the production of organic amino compounds, wherein an organic compound is first reacted with $NO_x$ and/or nitric acid to form an organic nitro compound with the formation of an $NO_x$-containing waste gas stream and the organic nitro compound is converted to the organic amino compound by means of a hydrogen-containing reaction gas, the reaction of the organic nitro compound with the hydrogen-containing reduction gas taking place wish the formation of a hydrogen-containing waste gas stream.

Amines are typical precursors of isocyanates, which are used in the production of formulations for PUR/PIR foams. They are produced by nitration of hydrocarbons, followed by catalytic reduction with hydrogen. In the production of aromatic amines, the nitration of the aromatics used as starting substance is generally carried out with nitric acid. Nitrogen oxides such as NO, $NO_2$ and also $N_2O$, referred to below for the sake of simplicity as $NO_x$, for which very low emission limits have to be observed, are obtained as a by-product here as a result of oxidation reactions. These waste gases therefore have to be treated before they can be released into the environment.

The thermal reduction of nitrogen oxides with natural gas is known from the fuel staging process and is described in Kolb, T., Jansohn, P., & Leuckel, W. (1988). Reduction of $NO_x$ Emissions in Turbulent Combustion by Fuel-Staging/Effects of Mixing and Stoichiometry in the Reduction Zone, Proceedings of the Combustion Institute, 22, p. 1193-1203, and in Greul, U. (1998), Experimentelle Untersuchung feuerungstechnischer $NO_x$-Minderungsmaßnahmen bei der Kohlenstaubverbrennung. Düsseldorf: VDI Verlag GmbH, pages 140-145. In this process, natural gas is generally added to a flue gas that has significant concentrations of $NO_x$. The nitrogen oxides obtained during combustion are converted to molecular nitrogen and intermediate components (HCN and $NH_3$) here by adding a fuel (generally methane, natural gas or coal) under reducing conditions. Burnout then takes place by a further addition of combustion air. Depending on process control, the optimum process conditions, such as the degree of the reducing conditions relative to the required residence time, vary with air-fuel ratios of 0.7 to 0.95 being established in the reduction zone in relation to the main combustion zone (Greul, 1998, see above).

Another method for the treatment of waste gases from nitration is oxidation with air and parallel absorption in water of the $NO_2$ formed to give aqueous nitric acid (Reference Document on Best Available Techniques for the Manufacture of Large Volume Inorganic Chemicals—Ammonia, Acids and Fertilisers, European Commission, August 2007, pages 97-99, 117-120, 135-136). This process is used for the production of nitric acid on an industrial scale, hut is costly and, because of the volatile compounds comprised in the waste gas from nitration, is only suitable when combined with an oxidising combustion. The nitric acid obtained is advantageously recycled into the nitration process.

A less technically complex alternative is absorption in more chemically reactive systems, such as dilute sodium hydroxide solution, but: this has the disadvantage that an additional waste substance is obtained which requires treatment.

Furthermore, the selective non-catalytic reduction (SNCR) of nitrogen oxides with ammonia or urea at temperatures of 800-1100° C. is known (Reference Document on Best Available Techniques for Large Combustion Plants, European Commission, July 2006, pages 106-114, 116). However, this method cannot be used efficiently for the waste gases from nitration in question since, with the high $NO_x$ concentrations in the waste gases, the exothermicity of the reduction reaction, e.g. according to the following reaction equation

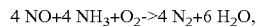

$$4\ NO+4\ NH_3+O_2 \rightarrow 4\ N_2+6\ H_2O,$$

requires a multi-stage reduction with intermediate cooling. In addition, the desired limit values cannot be reliably met because of the limited efficiency of the SNCR method. As a result of the high exothermicity and the associated temperature increase, undesirable secondary reactions, such as the reaction $4\ NH_3+5\ O_2 \rightarrow 4\ NO+6\ H_2O$, gain significance and mean that this method cannot be applied efficiently. This method can therefore only be used for low $NO_x$ concentrations but not for waste gases from nitration.

Finally, it is known that tail gases occurring during nitric acid production, which still comprise traces of $NO_x$, can be reduced catalytically with ammonia. This method is referred to as "Selective Catalytic Reduction" (SCR). In order to obtain adequate catalytic activity, the catalyst has to be operated at an elevated temperature. It should be home in mind that the reduction is strongly exothermic, and so this technique has to be used with the customary adiabatic fixed bed reactors only at $NO_x$ concentrations that are significantly lower than those in waste gases from a nitration process. A multi-stage execution with intermediate cooling is costly in terms of apparatus and is therefore uneconomical for the present application.

The object of the present invention consisted in providing a more cost-effective method and apparatus for the at least partial elimination of nitrogen oxides that are formed during the production of nitroaromatics.

SUMMARY OF THE INVENTION

The present invention relates to a method for reducing the concentration of nitrogen oxides in waste gases released during the production of organic amino compounds, comprising:
(1) reacting an organic compound with $NO_x$ and/or nitric acid to form an organic nitro compound wherein an $NO_x$-containing waste gas stream is formed and the organic nitro compound is converted to the organic amino compound by means of a hydrogen-containing reaction gas, the reaction of the organic nitro compound with the hydrogen-containing reduction gas taking place with the formation of a hydrogen-containing waste gas stream.
(2) combining the $NO_x$-containing waste gas stream with the hydrogen-containing waste gas stream and/or an externally supplied hydrogen stream and
(3) reacting the $NO_x$-containing waste gas stream with the hydrogen-containing waste gas stream and/or an externally supplied hydrogen stream at a temperature of 800 to 1700° C. for the at least partial reduction of the $NO_x$ concentration.

The present invention also provides an apparatus for the production of organic amino compounds and reducing the concentration of nitrogen oxides in waste gases released during such production, comprising:
(a) a production apparatus for the production of organic amino compounds, the production apparatus comprising:

(a)(i) a first reaction device for reacting an organic compound with $NO_x$ and/or nitric acid to form an organic nitro compound with the formation of an $NO_x$-containing waste gas stream and the organic nitro compound discharged via (a)(ii) an intermediate product line exiting the first reaction device and the $NO_x$-containing waste gas stream discharged via (a)(iii) a nitrogen oxide line exiting the first reaction device, wherein the intermediate product line leads into (a)(iv) a second reaction device in which the organic, nitro compound is reduced by means of a hydrogen-containing reaction gas to form the organic amino compound with the formation of a hydrogen-containing waste gas stream; and (b) a reduction apparatus comprising:

(b)(i) a reduction chamber connected to the nitrogen oxide line, in which the $NO_x$-containing waste gas stream can he combined with the hydrogen-containing waste gas stream fed in via (b)(ii) a reducing agent line (3) leading into the reduction chamber (2) and/or with (b)(iii) an externally supplied hydrogen stream;

wherein the reduction chamber is operated at a temperature of 800 to 1700° C. for the at least partial reduction of the $NO_x$ concentration.

BRIEF DESCRIPTION OF THE DRAWING

FIG. 1 is a schematic layout of a reduction apparatus according to the invention.

DETAILED DESCRIPTION OF THE PREFERRED EMBODIMENTS

The present invention is based on the finding that the hydrogen-rich waste gas stream obtained during the hydrogenation of the organic nitro compounds can be separated out and reacted with the $NO_x$-containing waste gas stream. In this way, not only are the nitrogen oxides, such as NO, $NO_2$ and $N_2O$, eliminated from the $NO_x$-containing waste gas stream but at the same time the quantity of the hydrogen-containing waste gas stream obtained, which would otherwise require separate disposal, e.g. by combustion, is reduced. The hydrogen-containing waste gas stream often comprises other volatile by-products of the hydrogenation reaction in addition to hydrogen, such as e.g. ammonia or aliphatic amines, which can also react with the nitrogen oxides at the reaction temperatures according to the invention.

Depending on how high the hydrogen concentration is in the hydrogen-containing waste gas stream, the method according to the invention can be implemented without the use of additional sources of energy, such as natural gas, although it is quite possible to use additional fuels of this type, particularly in order to improve the reduction of the nitrogen oxides further.

In a further embodiment of the method according to the invention, the externally supplied hydrogen stream consists of hydrogen. Within the framework of the present invention, this is understood to mean that the hydrogen stream consists of at least 70 vol. % pure hydrogen, preferably at least 80 vol. %, in particular at least 95 vol. % or even at least 98 vol. %. For this purpose it is possible to use e.g. technical-grade hydrogen.

Advantageously, the hydrogen-containing waste gas stream consists of at least 70 vol. % pure hydrogen, preferably at least 80 vol. %.

In a further embodiment of the method according to the invention, the organic compound is an aromatic compound, in particular aniline, benzene, monochlorobenzene, toluidine, nitrobenzene, mononitrotoluene and/or dinitrotoluene, the amino compounds produced in the method being used in particular for the production of isocyanate compounds, preferably for the production of aromatic polyisocyanates.

It is further provided in the method according to the invention that the hydrogen-containing waste gas stream encompasses by-products carrying amino groups, in particular aliphatic and/or aromatic amines and/or ammonia. This is advantageous because the said by-products also react with nitrogen oxides at the reaction temperatures according to the invention and reduce them, and so not only are these by-products used for reducing the concentration of nitrogen oxides but also, at the same time, the need to dispose of them is avoided.

As already set out above, the reduction of the nitrogen oxides can take place by the hydrogen-containing waste gas stream and/or externally supplied hydrogen. In an advantageous embodiment, however, one or more hydrocarbon compounds, in particular a hydrocarbon-containing gas, are added to the $NO_x$-containing waste gas stream before or during step (2) or during or after step (3) for the further reduction of the NC concentration, i.e., the hydrocarbon compound can be added before, during and/or after the reaction of the $NO_x$-containing waste gas stream with the hydrogen-containing waste gas stream and/or the externally supplied hydrogen stream. To this end, the hydrocarbon compound can be added to one or more of the feed lines for the hydrogen-containing waste gas stream and/or the externally supplied hydrogen stream. It is, however, also possible to add the hydrocarbon compound via a separate feed line.

In addition, it can be provided that air, oxygen-containing waste gases and/or oxygen are fed in in addition to the hydrocarbon compound and hydrogen-containing gas. This can be carried out either through one or more of the feed lines for the $NO_x$-containing waste gas stream. It is, however, preferred to feed in the air, oxygen-containing waste gases and/or oxygen through separate feed lines.

In this embodiment, in a further preferred manner, the $NO_x$ concentration can be determined during the reaction of the $NO_x$-containing waste gas stream with the hydrogen-containing waste gas stream and/or the externally supplied hydrogen stream and optionally the hydrocarbon compound, and the metering of the hydrocarbon compound can be controlled as a function of the measured reaction temperature and/or the $NO_x$ concentration. For this purpose, sensing probes that are known per se are used, the measurement signals of which are processed in an evaluation unit and used to control regulators for the metering.

In the method according to the invention, a temperature of 800 to 1700° C. is set for $NO_x$ reduction. The reaction of the $NO_x$-containing waste gas stream with the hydrogen-containing waste gas stream and/or the externally supplied hydrogen stream and optionally the hydrocarbon compound preferably takes place at a temperature of 1000 to 1700° C., in particular at 1100 to 1600° C., preferably at 1300 to 1600° C.

In a further embodiment of the method according to the invention, the reaction of the $NO_x$-containing waste gas stream with the hydrogen-containing waste gas stream and/or the externally supplied hydrogen stream takes place with a hyperstoichiometrie amount of substance of hydrogen, the excess hydrogen then being partially or completely oxidised with air and/or oxygen. In the present case, hyperstoichiometric is understood to mean that the quantity of hydrogen fed in is about 10 to 70 mole % more than the amount of substance theoretically needed for complete reduction. In this way, the chemical equilibrium can be shifted more strongly to the side of reduction. Furthermore, the hydrogen excess also has a positive effect on the reaction kinetics in terms of reduction. Under these hyperstoichiometrie conditions in relation to hydrogen, reactive nitrogen-containing intermediates are formed (e.g. $NH_3$ or, if hydrocarbons are added, also HCN), some of which are converted to nitrogen oxides during the subsequent oxidation of the excess hydrogen but at concentrations well below the initial concentration of the nitrogen oxides in the waste gas from nitration. In a downstream step, a reduction of these residual concentrations can take place by adding ammonia, ammonium hydroxide or urea; this partial step can be carried out by means of the known SNCR or SCR method.

Furthermore in the method according to the invention, the heat of reaction released during the reaction of the $NO_x$-containing waste gas stream with the hydrogen-containing waste gas stream and/or the externally supplied hydrogen stream, and/or the heat of reaction released while the excess hydrogen is reacted off, can be recovered. This can take place e.g. with the aid of heat exchangers.

The present invention also provides a reduction apparatus for reducing the concentration of nitrogen oxides in waste gases released during the production of organic amino compounds, wherein the reduction apparatus can be connected to a production apparatus for the production of organic amino compounds encompassing a first reaction device for reacting an organic compound with $NO_x$ and/or nitric acid to form an organic nitro compound with the formation of an $NO_x$-containing waste gas stream and the organic nitro compound can be discharged via an intermediate product line exiting the first reaction device and the $NO_x$-containing waste gas stream can be discharged via a nitrogen oxide line exiting the first reaction device, wherein the intermediate product line leads into a second reaction device, in which the organic nitro compound can be reduced by means of a hydrogen-containing reaction gas to form the organic amino compound with the formation of a hydrogen-containing waste gas stream, the reduction apparatus being characterised in that the reduction apparatus encompasses a reduction chamber connected to the nitrogen oxide line, in which the $NO_x$-containing waste gas stream can be combined with the hydrogen-containing waste gas stream fed in via a reducing agent line leading into the reduction chamber and/or with an externally supplied hydrogen stream and reacted at a temperature of 800 to 1700° C. for the at least partial reduction of the $NO_x$ concentration.

According to a preferred embodiment of the reduction apparatus according to the invention, in addition to the $NO_x$-containing waste gas stream to be reduced, a hydrocarbon compound, air, oxygen-containing waste gases and/or oxygen is fed into the reduction chamber, in particular via the reducing agent line or a separate feed line. To control the metering of the hydrocarbon compound, as mentioned above, an appropriate measuring and control arrangement can be used.

According to a development of the reduction apparatus according to the invention, the reduction chamber is equipped with a burner or a burner is provided upstream of the reduction chamber, wherein the reducing agent line and/or the feed line for hydrocarbon compound, air and/or oxygen preferably leads into the burner. The specified temperatures for the reduction can be achieved with the aid of the burner.

A burner device can be provided upstream of the reduction chamber, encompassing a burner, a combustion chamber and optionally a reduction device, wherein air, oxygen-containing waste gases and/or oxygen can be supplied to the burner of the burner device via a combustion air line. The reduction chamber and the burner device can be directly connected in series or can also be coupled together by a connecting line. Between the reduction chamber and the burner device, intermediate cooling can be provided which makes it possible to utilise the heat of reaction by means of a connected heat exchanger and/or steam generator.

The reduction device can advantageously encompass an SNCR stage, in which case an ammonia line also leads into the reduction device, through which ammonia, urea and/or another ammonia-releasing substance can be fed. As a result of this measure, any nitrogen oxides formed as by-products during hydrogen oxidation can be removed again. As an alternative to the SNCR stage, a downstream SCR stage can be provided. This is typically operated at lower temperatures but requires the use of an appropriate catalyst.

In a particularly advantageous embodiment of the reduction apparatus according to the invention, a waste heat utilisation device, in particular a heat exchanger, is assigned to the reduction chamber and/or the burner device. As a result, the heat of reaction released can be utilised in a meaningful way by being used e.g. for steam generation, preheating the substances used or for other processes.

Finally, a gas scrubbing device can be provided downstream of the burner device, in which the waste gases are scrubbed before being discharged via a chimney. As a result, final residues of harmful substances, such as traces of ammonia, nitrogen oxides and the like, can be removed from the waste gas stream.

The present invention further relates to the use of a hydrogen-containing waste gas stream and/or of hydrogen for reducing the concentration of nitrogen oxides in waste gases released during the production of organic amino compounds, in particular in a method for the production of aromatic polyisocyanates.

In an advantageous embodiment of the use according to the invention, the hydrogen-containing waste gas stream is formed partially or completely by a hydrogen-containing waste gas stream that develops during the conversion of an organic nitro compound to an organic amino compound by means of a hydrogen-containing reaction gas.

The present invention is explained in more detail below with the aid of an exemplary embodiment illustrated in FIG. 1, wherein FIG. 1 shows a schematic layout of a reduction apparatus according to the invention.

The schematic layout of a reduction apparatus according to the invention is shown in FIG. 1, The reduction apparatus is used for reducing the concentration of nitrogen oxides in waste gases released during the production of organic amino compounds, with the possibility of the reduction apparatus being connected to a production apparatus for the production of organic amino compounds, which is not illustrated here. This production apparatus, which encompasses e.g. a first reaction device (not illustrated here) for reacting an organic compound with $NO_x$ and/or nitric acid to form art organic nitro compound with the formation of an $NO_x$-containing waste gas stream, wherein the organic nitro compound can be discharged via an intermediate product line exiting the first reaction device and the $NO_x$-containing waste gas stream can be discharged via a nitrogen oxide line 1 exiting the first reaction device. The intermediate product lSine leads into a second reaction device (not illustrated here), in which the organic nitro compound can be reduced by means of a hydrogen-containing reaction gas to form the organic amino compound with the formation of a hydrogen-containing waste gas stream.

Connected to the nitrogen oxide line 1, the reduction apparatus encompasses a reduction chamber 2 in which the $NO_x$-containing waste gas stream can be combined with the hydrogen-containing waste gas stream fed in via a reducing agent line 3 leading into the reduction chamber 2 and/or with an externally supplied hydrogen stream, and reacted at a temperature of 800 to 1700° C. for the at least partial reduction of the $NO_x$ concentration.

Furthermore, a hydrocarbon compound, air, oxygen-containing waste gases and/or oxygen can be fed into the reduction chamber 2. This takes place here via a separate feed fine 6 and optionally via a combustion air line 4. A burner 5 is provided upstream of the reduction chamber 2, the reducing agent line 3 and/or the feed line 4 for hydrocarbon compound, air and/or oxygen leading into the burner 5. The reduction chamber 2 additionally encompasses a waste heat utilisation device 13 in the form of a heat exchanger arranged at the outlet side thereof to recover the heat released during the reaction.

Downstream of the reduction chamber 2 and connected thereto, a burner device 7 is arranged which encompasses a burner 8, a combustion chamber 9 and a reduction device 30. Air, oxygen-containing waste gases and/or oxygen can be supplied to the burner 8 of the burner device 7 via a combustion air line 11. An ammonia line 12, through which ammonia, urea and/or another ammonia-releasing substance can be fed, leads into the reduction device 10. A waste heat utilisation device 14, here a heat exchanger is assigned to the burner device 7 on the outlet side.

Downstream of the burner device 7, a gas scrubbing device 15 is provided, from where the waste gases that have been purified and freed from nitrogen oxides are discharged into the environment through a chimney 16.

LIST OF REFERENCE SIGNS (1) Nitrogen oxide line
(2) Reduction chamber
(3) Reducing agent line
(4) Combustion air line/Separate feed line
(5) Burner
(6) Separate feed line
(7) Burner device
(8) Burner
(9) Combustion chamber
(10) Reduction device
(11) Combustion air line
(12) Ammonia line
(13) Waste heat utilisation device
(14) Waste heat utilisation device
(15) Gas scrubbing device
(16) Chimney Although the invention has been described in detail in the foregoing for the purpose of illustration, it is to be understood that such detail is solely for that purpose and that variations can be made therein by those skilled in the art without departing from the spirit and scope of the invention except as it may be limited by the claims.

The invention claimed is:

1. A method for reducing the concentration of nitrogen oxides in waste gases released during the production of organic amino compounds, comprising:

(1) reacting an organic compound with $NO_x$ and/or nitric acid to form an organic nitro compound wherein an $NO_x$-containing waste gas stream is formed and the organic nitro compound is converted to the organic amino compound by means of a hydrogen-containing reaction gas, the reaction of the organic nitro compound with the hydrogen-containing reduction gas taking place with the formation of a hydrogen-containing waste gas stream, (2) combining the $NO_x$-containing waste gas stream with the hydrogen-containing waste gas stream and/or an externally supplied hydrogen stream, and (3) reacting the $NO_x$-containing waste gas stream with the hydrogen-containing waste gas stream and/or an externally supplied hydrogen stream at a temperature of 800 to 1700° C. for the at least partial reduction of the $NO_x$ concentration.

2. The method according to claim 1, wherein the externally supplied hydrogen stream consists of at least 70 vol. % pure hydrogen, the externally supplied hydrogen stream comprising technical-grade hydrogen.

3. The method according to claim 1, wherein the hydrogen-containing waste gas stream consists of at least 70 vol. % pure hydrogen.

4. The method according to claim 1, wherein the organic compound is an aromatic compound.

5. The method according to claim 4, wherein the organic compound is selected from the group consisting of aniline, benzene, monochlorobenzene, toluidine, nitrobenzene, mononitrotoluene and dinitrotoluene.

6. The method according to claim 3, wherein the hydrogen-containing waste gas stream comprises by-products carrying amino groups.

7. The method according claim 1, further comprising reducing the $NO_x$ concentration further by adding one or more hydrocarbon compounds to the $NO_x$-containing waste gas stream before or during step (2) or during or after step (3).

8. The method according to claim 7, wherein the hydrocarbon compound is added before, during and/or after the reaction of the $NO_x$-containing waste gas stream with the hydrogen-containing waste gas stream and/or the externally supplied hydrogen stream.

9. The method according to claim 7, further comprising determining the $NO_x$ concentration during the reaction of the $NO_x$-containing waste gas stream with the hydrogen-containing waste gas stream and/or the externally supplied hydrogen stream and optionally controlling the hydrocarbon compound and the metering of the hydrocarbon compound as a function of the measured reaction temperature and/or the $NO_x$ concentration.

10. The method according to claim 1, further comprising adding air, oxygen-containing waste gases and/or oxygen to the $NO_x$-containing waste gas stream before or during step (2) or during or after step (3).

11. The method according to claim 1, wherein the reaction of the $NO_x$-containing waste gas stream with the hydrogen-containing waste gas stream and/or the externally supplied hydrogen stream and optionally the hydrocarbon compound takes place at a temperature of 1000 to 1700° C.

12. The method according to claim 1, wherein the reaction of the $NO_x$-containing waste gas stream with the hydrogen-containing waste gas stream and/or the externally supplied hydrogen stream takes place with a hyperstoichiometrie amount of substance of hydrogen and further comprising at least partially oxidizing the excess hydrogen with air and/or oxygen.

13. The method according to claim 12, further comprising adding a compound selected from the group consisting of ammonia, urea and/or another ammonia-releasing compound to the $NO_x$-containing waste gas stream.

14. The method according to claim 1, further comprising recovering at least a portion of any heat of reaction released during the reaction of the $NO_x$-containing waste gas stream with the hydrogen-containing waste gas stream and/or the externally supplied hydrogen stream, and/or any heat of reaction released while the excess hydrogen is reacted off, with the aid of heat exchangers.

* * * * *